United States Patent [19]

Suto et al.

[11] Patent Number: 5,296,601

[45] Date of Patent: Mar. 22, 1994

[54] PROCESS FOR PRODUCING CARBOXYLIC ACID ESTERS

[75] Inventors: Keiji Suto, Nishinomiya; Masaaki Kudo, Kadoma; Moriharu Yamamoto, Kobe, all of Japan

[73] Assignee: Nihon Nohyaku Co., Ltd., Tokyo, Japan

[21] Appl. No.: 888,618

[22] Filed: May 27, 1992

Related U.S. Application Data

[62] Division of Ser. No. 528,919, May 29, 1990, Pat. No. 5,142,057.

[30] Foreign Application Priority Data

Mar. 12, 1987 [JP] Japan .................. 62-57431
Feb. 13, 1988 [JP] Japan .................. 63-31139

[51] Int. Cl.$^5$ ............ C07C 69/76; C07C 69/84; C07C 317/14; C07C 241/44; C07C 213/55
[52] U.S. Cl. .................. 544/355; 546/170; 546/318; 546/319; 546/321; 546/335; 549/71; 549/484; 549/485; 549/486; 560/11; 560/12; 560/21; 560/59; 560/64; 560/65; 560/67; 560/102
[58] Field of Search .............. 546/170, 321, 318, 319, 546/335; 558/416; 549/71, 484, 485, 486; 544/355; 560/11, 59, 52, 67, 64, 65, 67, 102, 12, 21

[56] References Cited

U.S. PATENT DOCUMENTS 3,988,358 10/1976 Heck .................. 546/317
4,128,554 12/1978 Heck .................. 546/317

FOREIGN PATENT DOCUMENTS 57-200338 12/1982 Japan .................. 560/114
61-293950 12/1986 Japan .................. 560/114

OTHER PUBLICATIONS

J. Org. Chem. 1981, vol. 46 pp. 4614-4617 (No. 22).

Primary Examiner—Alan L. Rotman
Attorney, Agent, or Firm—Cushman, Darby & Cushman

[57] ABSTRACT

A process for producing a carboxylic acid ester, which comprises reacting an organic chloride having at least one chlorine atom on its ring of a substituted or unsubstituted, aromatic or heterocyclic hydrocarbon with carbon monoxide and an amine or an alcohol in the presence of a base by using as catalysts a palladium compound and a phosphine compound represented by the general formula (V):

$$(R)_2P-X-P(R)_2 \qquad (V)$$

wherein R is an alkyl group or a substituted or unsubstituted phenyl group, and X is an alkylene group having 1 to 6 carbon atoms,

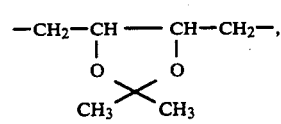

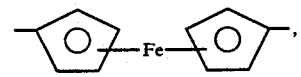

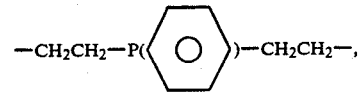

or a binaphthyl group.

7 Claims, No Drawings

PROCESS FOR PRODUCING CARBOXYLIC ACID ESTERS

This is a division of application Ser. No. 07/528,919, filed May 29, 1990, now U.S. Pat. No. 5,142,057.

FIELD OF THE INVENTION AND RELATED ART STATEMENT

This invention relates to a process for producing an aromatic or heterocyclic carboxylic acid amide or ester.

More particularly, it relates to a process for producing a carboxylic acid amide represented by the general formula (I-1):

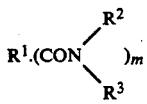  (I-1)

(wherein $R^1$ is a substituted or unsubstituted, aromatic or heterocyclic hydrocarbon group; $R^2$ and $R^3$, which may be the same or different, are hydrogen atoms or substituted or unsubstituted, aliphatic, aromatic or heterocyclic hydrocarbon groups, or are alkylene groups bonded to each other through an oxygen atom or a nitrogen atom; and m is an integer of 1 or more) or a carboxylic acid ester represented by the general formula (I-2):

  (I-2)

(wherein $R^1$ and m have the same meanings as defined above, and $R^4$ is a substituted or unsubstituted, aliphatic, aromatic or heterocyclic hydrocarbon group), which comprises reacting an organic chloride represented by the general formula (IV):

  (IV)

(wherein $R^1$ and m have the same meanings as defined above) with carbon monoxide and an amide represented by the general formula (III):

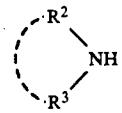  (III)

(wherein $R^2$ and $R^3$ have the same meanings as defined above) or an alcohol represented by the general formula (II):

  (II)

(wherein $R^4$ has the same meaning as defined above) in the presence of a base by using as catalysts a palladium compound and a phosphine compound represented by the general formula (V):

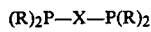  (V)

(wherein R is an alkyl group or a substituted or unsubstituted phenyl group, and X is an alkylene group having 1 to 6 carbon atoms,

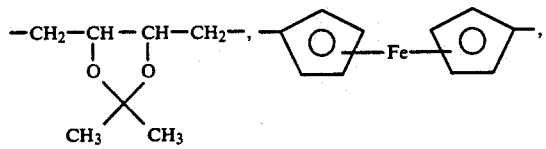

or a binaphthyl group).

The present invention provides a novel process for producing carboxylic acid amides or esters which are per se useful as agricultural chemicals and carboxylic acid amides which are useful in the fields of medicines, etc.

RELATED ART DISCUSSION

As processes for producing aromatic or heterocyclic acid amides or esters, there have so far been disclosed processes comprising reacting an aromatic or heterocyclic halide and a primary or secondary amine with carbon monoxide in the presence of palladium/triarylphosphine (see the specifications of U.S. Pat. Nos. 3988358 and 4128554).

However, these processes employ a reaction with an iodide or a bromide as the aromatic halide, but not a reaction with an aromatic chloride. As a reaction of a chloride, the above prior art references disclose only a reaction of highly reactive 2-chloropropene having a double bond with aniline under pressure in the presence of a tertiary amine which yields N-phenyl-methacrylamide, and do not disclose a reaction of an aromatic chloride at all. Moreover, the phosphine compound used as a catalyst in the above processes is a triarylphosphine which is utterly different from the phosphine compound used in the present invention.

There is also known a process comprising reacting an organic halide, carbon monoxide and phosphoric acid triamide with one another in the presence of a carbonylation catalyst (Jap. Pat. Appln. Kokai (Laid-open) No. 57-200338). However, this process is not used at all for a reaction with an aromatic chloride having a chlorine atom directly bonded to the aromatic ring as a substituent, and moreover it uses a phosphoric triamide. This phosphoric triamide is expensive and very toxic, so that it is not suitable for industrial use from the viewpoint of industrial hygiene.

Jap. Pat. Appln. Kokai (Laid-Open) No. 61-293950 disclosed a process for producing a carboxylic acid and an ester thereof using a chloro- or bromo-allenecarbonylchromium compound, but the production cost of the tricarbonylchronium complex itself, which is used therein as a reaction substrate, is per se high and this process is disadvantageous also from the viewpoint of toxicity.

As described above, the reactions of aromatic iodides or bromides with carbon monoxide are known, but there is known no process in which an aromatic carboxylic acid amide or ester is synthesized by the reaction of an aromatic chloride with carbon monoxide.

SUMMARY OF THE INVENTION

In consideration of such conditions, the present inventors earnestly investigated the reactions of aromatic or heterocyclic chlorides with carbon monoxide and consequently established a process for producing an aromatic or heterocyclic carboxylic acid amide or ester in a high yield, whereby the present invention has been accomplished.

DETAILED DESCRIPTION OF PREFERRED EMBODIMENTS

The reaction of this invention can be schematically represented, for example, as follows:

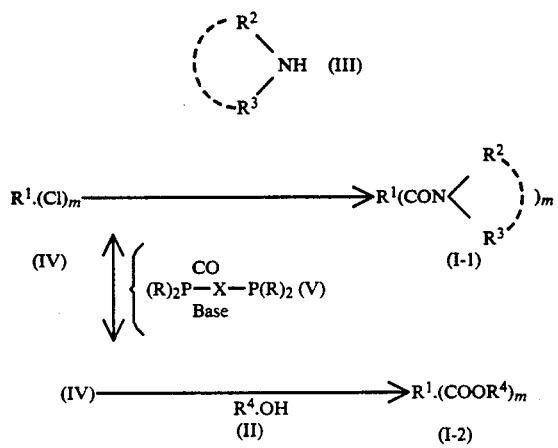

wherein R, $R^1$, $R^2$, $R^3$, $R^4$, m and X have the same meanings as defined above.

As the substituent on $R^1$, there may be exemplified alkyl groups, alkyloxy groups, halogen atoms, haloalkyl groups, alkoxycarbonyl groups, alkoxy-carbonylalkyl groups, sulfonic acid group, etc. Although m depends on the kind of the aromatic group or the heterocyclic ring, m is usually 1 to 10.

That is to say, an organic chloride of the general formula (IV) is reacted with carbon monoxide and an amine of the general formula (III) or an alcohol of the general formula (II) in the presence of a base in the presence or absence of a solvent by using a palladium compound and a phosphine compound of the general formula (V) as catalysts, whereby a desired carboxylic acid amide of the general formula (I-1) or a desired carboxylic acid ester of the general formula (I-2) can be produced.

The organic chloride of the general formula (IV) used in this invention may be any one so long as it has at least one chlorine atom on its ring of a substituted or unsubstituted, aromatic or heterocyclic hydrocarbon. It includes also fused ring hydrocarbons and fused heterocyclic ring hydrocarbons. Typical examples of said organic chloride includes, for example, aromatic organic chlorides such as chlorobenzene, dichlorobenzene, trichlorobenzene, tetrachlorobenzene, pentachlorobenzene, hexachlorobenzene, chlorofluorobenzene, chlorodifluorobenzene, chlorotrifluorobenzene, chlorotetrafluorobenzene, chloropentafluorobenzene, trifluoromethylchlorobenzene, chlorotoluene, dichlorotoluene, trichlorotoluene, tetrachlorotoluene, pentachlorotoluene, ethylchlorobenzene, chlorocumene, chloromesitylene, dichloromesitylene, chloroxylene, dichloroxylene, trichloroxylene, tetrachloroxylene, chlorophenol, dichlorophenol, trichlorophenol, chloroanisole, dichloroanisole, trichloroanisole, chlorodimethoxybenzene, chlorotrimethoxybenzene, chloromethylenedioxybenzene, chlorophenoxyphenol, chlorobenzoylphenol, chlorobenzenesulfonylphenol, chloronitrobenzene, dichloronitrobenzene, chlorocyanobenzene, chlorophenylacetic acid esters, N-acetylchloroaniline, chlorophenoxyaniline, chlorobenzoylaniline, chlorobenzenesulfonylaniline, chloroacetophenone, chlorobenzophenone, chloromethylthiobenzene, chlorobenzoic acid esters, chlorodiphenyl ether, benzyloxychlorobenzene, chlorophenylbutoxybenzene, dichlorodiphenyl ether, dichlorobenzophenone, dichlorodiphenylmethane, dichlodiphenyldifluoromethane, dichlorodiphenylhexafluoropropane, dichlorodiphenyl sulfide, dichlorodiphenyl sulfoxide, dichlorodiphenyl sulfone, dichlorobiphenyl, tetrachlorodiphenyl ether, tetrachlorobenzophenone, tetrachlorodiphenylmethane, tetrachlorodiphenyldifluoromethane, tetrachlorodiphenylhexafluoropropane, tetrachlorodiphenyl sulfide, tetrachlorodiphenyl sulfoxide, tetrachlorodiphenyl sulfone, tetrachlorobiphenyl, chloronaphthalene, dichloronaphthalene, trichloronaphthalene, chloromethylnaphthalene, chloroanthraquinone, and the like; and heterocyclic organic chlorides such as chlorothiophene, dichlorothiophene, chlorofuran, chloroindole, dichloroindole, chloropyridine, dichloropyridine, chlorotrifluoromethylpyridine, chloropicoline, dichloropicoline, chloroquinoline, dichloroquinoline, trichloroquinoline, chloroquinoxaline, dichloroquinoxaline, and the like. The organic chloride may be used in a predetermined amount only as a reactant, or it may be added in excess and used both as a reactant and a solvent.

The amine of the general formula (III) used in this invention includes, for example, ammonia; aliphatic amines such as methylamine, ethylamine, dimethylamine, diethylamine, and the like; aromatic amines such as aniline, alkylanilines, haloanilines, haloalkylanilines, alkoxyanilines (methoxyaniline, ethoxyaniline and isopropoxyaniline), benzylamine, and the like; and heterocyclic amines such as pyrrole, imidazole, triazole, indole, aminopyridine, aminotriazole, aminoimidazole, aminothiophene, aminothiazole, aminofuran, aminobenzimidazole, aminoquinoline, and the like.

The alcohol of the general formula (II) used in this invention includes, for example, aliphatic alcohols such as reethanol, ethanol, propanol, butanol, and the like; aromatic alcohols such as phenol, halophenols, cresol, xylenol, benzyl alcohol, cinnamyl alcohol and the like; and heterocyclic hydroxides such as furfuryl alcohol, thienyl alcohol, and the like. The alcohol may be used either as such in a predetermined amount or in the form of a previously prepared alcoholate.

It is sufficient that the amine of the general formula (III) or the alcohol of the general formula (II) is present in the reaction system in an amount equimolar with the organic chloride (or in an amount of a number of moles corresponding to the chlorine atoms on the ring of the organic chloride) or in excess of the organic chloride.

The amine of the general formula (III) can be allowed to act also as a base by use in excess.

The palladium compound as catalyst in this invention is used in combination with a phosphine compound. The palladium compound includes, for example, metallic palladium, palladium carbon, palladium alumina, palladium chloride, palladium bromide, palladium acetate, dichlorobiscyanophenylpalladium, dichlorobistriphenylphosphine palladium, tetrakistriphenylphosphine palladium, etc.

As the phosphine compound of the general formula (V) which can be used in combination with the palladium compound in this invention, there may be exemplified bis(dialkylphosphino)alkanes such as 1,1-bis(-dimethylphosphino)methane, 1,1-bis(diethylphosphino)methane, 1,2-bis(dimethylphosphino)ethane, 1,2-bis(diethylphosphino)ethane, 1,3-bis(dimethylphosphino)propane, 1,4-bis(dimethylphosphino)butane, and the like, 1,1-bis(diphenylphosphino)methane, 1,2-bis(diphenylphosphino)ethane, 1,3-bis(diphenylphosphino)propane, 1,4-bis(diphenylphosphino)butane, 1,5-bis(diphenylphosphino)pentane, 1,6-bis(diphenylphosphino)hexane, 2,3-0-isopropylidene-2,3-dihydroxy-1,4-bisdiphenylphosphinobutane, bisdiphenylphosphinoferrocene, bisdiphenylphosphinobinaphthyl, 1,2-bis(diphenylphosphino)benzene, 1,1-bis(dibenzophosphoryl)methane, 1,2-bis(dibenzophosphoryl)ethane, 1,3-bis(dibenzophosphoryl)propane, 1,4-bis(dibenzophosphoryl)butane, 1,5-bis(dibenzophosphoryl)pentane, etc.

The adding amount of the phosphine compound is 0.01 to 10,000 moles, preferably 0.1 to 100 moles per mole of the palladium compound.

In this invention, the palladium compound and the phosphine compound of the general formula (V) are used in combination and may be used in the reaction system either individually or in the form of a previously prepared complex.

Although not critical, the total amount of the palladium compound and the phosphine compound added to the reaction system is 0.0001 to 0.5 mole, preferably 0.001 to 0.1 mole per mole of the organic chloride of the general formula (IV).

As the base usable in this invention, there may be exemplified those selected from either inorganic bases or organic bases, for example, inorganic bases such as sodium carbonate, potassium carbonate, sodium hydroxide, potassium hydroxide, and the like; and organic bases such as triethylamine, tributylamine, diisopropylethylamine, triisooctylamine, pyridine, N-methylpyrrolidine, N-methylmorpholine, N-ethylmorpholine, and the like.

Although the base is used preferably in an amount required for neutralization of hydrogen chloride generated, the using amount may, of course, be smaller or larger than this amount.

The reaction in this invention can be carried out in the presence or absence of a solvent, and any solvent can be used so long as it does not inhibit the reaction seriously. As such a solvent, there may be exemplified, for example, organic solvents such as hexane, benzene, ether, tetrahydrofuran, acetonitrile, dimethylformamide, hexamethylphosphotriamide, acetone, and the like.

The reaction in this invention is carried out at atmospheric pressure or under pressure. The pressure of carbon monoxide is properly selected in the range of 1 to 200 atmospheres, preferably 1 to 50 atmospheres.

The reaction temperature in this invention is usually 100° to 300° C., preferably 150° to 250° C.

As a reactor used in this invention, a conventional one may be used. When the reaction is carried out under pressure, any reactor may be used so long as it can withstand the reaction pressure, and usually a reactor made of metal or glass is used.

Although varied depending on the amounts of the reactants and the reaction temperature, the reaction time is selected in the range of several minutes to 48 hours.

A desired compound can be obtained by treating the reaction mixture by a conventional method after completion of the reaction.

Examples and Comparative Examples of this invention are described below but are not by way of limitation but by way of illustration.

EXAMPLE 1

Production of 3'-isopropoxy-2-toluanilide

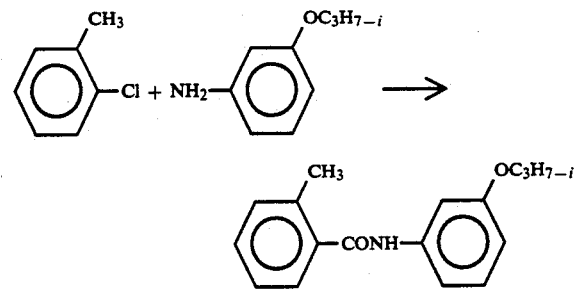

In an autoclave made of a metal were placed 12.7 g of ortho-chlorotoluene, 3 g of meta-isopropoxyaniline, 17.7 mg of palladium chloride, 426 mg of 1,4-bisdiphenylphosphinobutane and 23 g of sodium carbonate. The air in the autoclave was replaced with carbon monoxide introduced thereinto in several times, after which carbon monoxide was further introduced to adjust its pressure therein to 30 kg/cm$^2$. The internal temperature was adjusted to 200° C. on a salt bath and the reaction was carried out thereon with stirring for 5 hours. After completion of the reaction, the reaction mixture was cooled to room temperature and washed with water. Subsequently, the organic layer was separated, concentrated, and then recrystallized from ethyl acetatehexane to obtain 2.6 g of 3'-isopropoxy-2-toluanilide.

Melting point 92°–93° C., yield 2.6 g.

EXAMPLE 2

Production of 2-α,α,α-trifluorotoluanilide

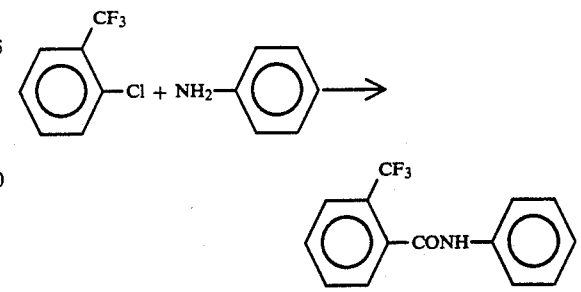

In an autoclave made of a metal were placed 18.06 g of ortho-chlorobenzotrifluoride, 1.86 g of aniline, 17.5 mg of palladium chloride, 426 mg of 1,4-bisdiphenylphosphinobutane and 2.3 g of sodium carbonate. The air in the autoclave was replaced with carbon monoxide introduced thereinto in several times, after which carbon monoxide was further introduced to adjust its pressure therein to 30 kg/cm$^2$. The internal temperature was adjusted to 200° C. on a salt bath and the reaction was carried out thereon with stirring for 3 hours. After completion of the reaction, the reaction mixture was cooled to room temperature and washed with water. Subsequently, the organic layer was separated and then concentrated to obtain 4.26 g of the desired compound 2-α,α,α-trifluorotoluanilide.

Melting point 145°–150° C., yield 4.26 g.

EXAMPLE 3

Production of 3'-isopropyl-2-α,α,α-trifluorotoluanilide

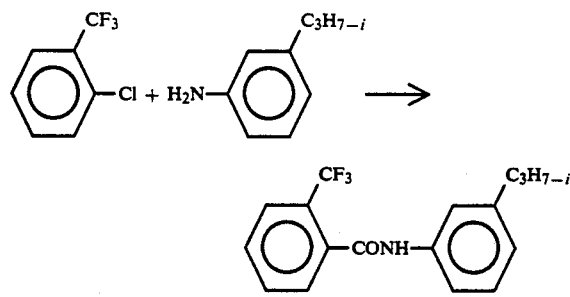

In an autoclave made of a metal were placed 18.1 g of ortho-chlorobenzotrifluoride, 2.7 g of metaisopropyl aniline, 17.5 mg of palladium chloride, 426 mg of 1,4-bisdiphenylphosphinobutane and 2.3 g of sodium carbonate. The air in the autoclave was replaced with carbon monoxide introduced thereinto in several times, after which carbon monoxide was further introduced to adjust its pressure therein to 30 kg/cm². The internal temperature was adjusted 2000° C. on a salt bath and the reaction was carried out thereon with stirring for 3 hours. After completion of the reaction, the reaction mixture was cooled to room temperature and washed with water. Subsequently, the organic layer was separated and then concentrated to obtain 3.0 g of the desired compound 3'-isopropyl-2-α,α,α-trifluorotoluanilide.

Melting point 88.90° C., yield 3.0 g.

EXAMPLE 4

Production of 3'-isopropoxy-2-α,α,α-trifluorotoluanilide

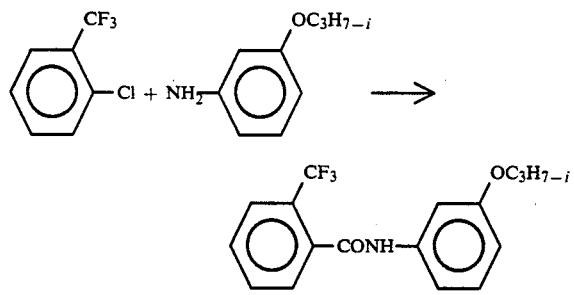

In an autoclave made of a metal were placed 18.1 g of ortho-chlorobenzotrifluoride, 3 g of metaisopropoxyaniline, 3.5 mg of palladium chloride, 85 mg of 1,4-bisdiphenylphosphinobutane and 2.3 g of sodium carbonate. The air in the autoclave was replaced with carbon monoxide introduced thereinto in several times, after which carbon monoxide was further introduced to adjust its pressure therein to 30 kg/cm². The internal temperature was adjusted to 200° C. on a salt bath and the reaction was carried out thereon with stirring for 5 hours. After completion of the reaction, the reaction mixture was cooled to room temperature and washed with water. Then, the organic layer was separated, whereby the desired substance 3'-isopropoxy-2-α,α,α-trifluorotoluanilide was obtained in a 79.3% yield as measured by a gas chromatography using triphenylmethane as an internal standard substance.

Melting point 102°–103° C., yield 79.3%.

EXAMPLE 5

Production of 3'-isopropoxy-4-α,α,α-trifluorotoluanilide

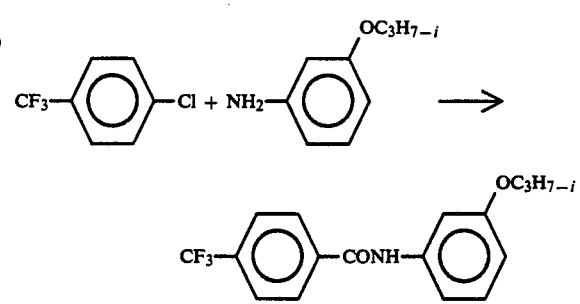

In an autoclave made of a metal equipped with an electromagnetic induction type stirrer were placed 18 ml of para-chlorobenzotrifluoride, 25 g of meta-isopropoxyaniline, 2.9 mg of palladium chloride, 0.15 g of 1,4-bisdiphenylphosphinobutane and 2.5 g of potassium carbonate. The air in the autoclave was replaced with carbon monoxide introduced thereinto in several times, after which carbon monoxide was further introduced to adjust its pressure therein to 25 kg/cm². The internal temperature was adjusted to 200° C. and the reaction was carried out thereon with stirring for 5 hours. After completion of the reaction, the reaction mixture was cooled to room temperature and washed with water. Subsequently, the organic layer was separated, concentrated, and then recrystallized from isopropanol-hexane to obtain 3.72 g of 3'-isopropoxy-4-α,α,α-trifluorotoluanilide.

Melting point 90°–92° C., yield 3.7 g.

EXAMPLE 6

Production of 3'-isopropoxy-2-α,α,α-trifluorotoluanilide

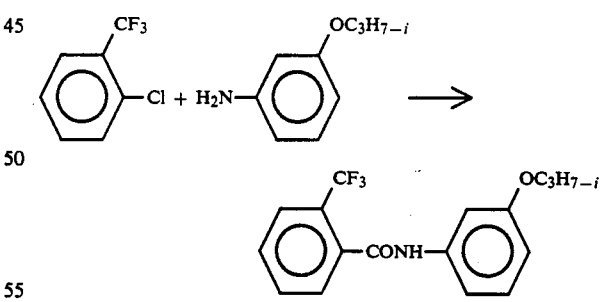

In an autoclave made of a glass equipped with an electromagnetic induction type stirrer were placed 90 g of ortho-chlorobenzotrifluoride, 15 g of metaisopropoxyaniline, 0.53 mg of 2% palladium carbon, 850 mg of 1,4-bisdiphenylphosphinobutane and 11.7 g of sodium carbonate. The air in the autoclave was replaced with carbon monoxide introduced thereinto in several times, after which carbon monoxide was further introduced to adjust its pressure therein to 20 kg/cm². The reaction was carried out thereon with stirring at an internal temperature of 200° C. for 5 hours. After completion of the reaction, the reaction mixture was cooled to room temperature and washed with water. Then, the organic layer was separated, whereby the desired substance 3'-isopropoxy-2-α,α,α-trifluorotoluanilide was obtained in a 84.5% yield as measured by a gas chromatography using triphenylmethane as an internal standard substance.

6-2

In an autoclave made of a metal were placed 18.1 g of ortho-chlorobenzotrifluoride, 3 g of metaisopropoxyaniline, 3.1 g of benzene, 5.3 mg of palladium bromide, 85 mg of 1,4-bisdiphenylphosphinobutane and 2.3 g of sodium carbonate. The air in the autoclave was replaced with carbon monoxide introduced thereinto in several times, after which carbon monoxide was further introduced to adjust its pressure therein to 30 kg/cm². The internal temperature was adjusted to 200° C. on a salt bath and the reaction was carried out thereon with stirring for 5 hours. After completion of the reaction, the reaction mixture was cooled to room temperature and washed with water. Then, the organic layer was separated, whereby the desired substance 3'-isopropoxy-2-α,α,α-trifluorotoluanilide was obtained in a 83.1% yield as measured by a gas chromatography using triphenylmethane as an internal standard substance.

6-3~5

3'-Isopropoxy-2-α,α,α-trifluorotoluanilide was produced under the same conditions as in Example 6-2, except that each palladium compound listed in the following table was used in place of palladium bromide. The results obtained are summarized in the table.

| Example | Palladium compound | Using amount (mg) | Yield (%) |
| --- | --- | --- | --- |
| 6-3 | PdCl₂(PhCN)₂ | 7.7 | 79.3 |
| 6-4 | PdCl₂(Ph₃P)₂ | 14 | 81.2 |
| 6-5 | Pd(Ph₃P)₄ | 23.1 | 8.4 |

6-6~7

3'-Isopropoxy-2-α,α,α-trifluorotoluanilide was produced under the same conditions as in Example 5-2, except that each phosphine compound listed in the following table was used in place of 1,4-bisdiphenylphosphinobutane. The results obtained are summarized in the table.

| Example | Phosphine compound | Using amount (mg) | Yield (%) |
| --- | --- | --- | --- |
| 6-7 | DPPE | 79 | 33.5 |
| 6-8 | DPPP | 82 | 49.6 |

DPPE: 1,2-bisdiphenylphosphinoethane
DPPP: 1,3-bisdiphenylphosphinopropane

EXAMPLE 7

Production of 4,4'-bis(31''-isopropoxyphenylcarbamoyl)benzophenone

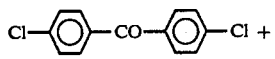

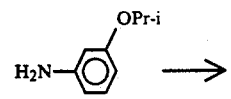

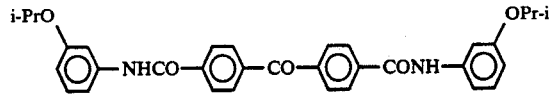

In an autoclave made of a metal were placed 3.75 g of 4,4'-dichlorobenzophenone, 4.53 g of metaisopropoxyaniline, 5.3 mg of palladium chloride, 127.8 mg of 1,4-bisdiphenylphosphinobutane, 3.18 g of sodium carbonate and 40 ml of dimethylacetamide. The air in the autoclave was replaced with carbon monoxide introduced thereinto in several times, after which carbon monoxide was further introduced to adjust its pressure therein to 30 kg/cm². The internal temperature was adjusted to 190° C. on a salt bath and the reaction was carried out thereon with stirring for 5 hours.

After completion of the reaction, the reaction mixture was cooled to room temperature and added to water, after which the deposited crystals were filtered and the residue was washed with water and dried. Thus, 3.81 g of the desired compound benzophenone was obtained.

Melting point 149°-151° C.

EXAMPLE 8

Production of nicotinic acid anilide

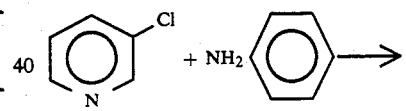

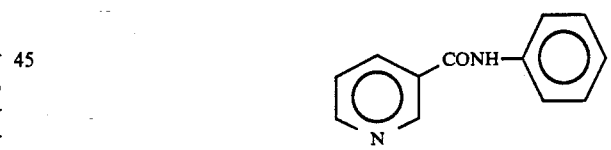

In an autoclave made of a metal were placed 6.75 g of 3-chloropyridine, 1.86 g of aniline, 7.81 g of benzene, 17.5 mg of palladium chloride, 426 mg of bisdiphenylphosphinobutane and 2.33 g of sodium carbonate. The air in the autoclave was replaced with carbon monoxide introduced thereinto in several times, after which carbon monoxide was further introduced to adjust its pressure therein to 30 kg/cm². The internal temperature was adjusted to 225° C. on a salt bath and the reaction was carried out thereon with stirring for 3 hours. After completion of the reaction, the reaction mixture was cooled to room temperature and washed with water. Subsequently, the organic layer was separated and then concentrated to obtain the desired compound nicotinic acid anilide.

Melting point 113°-119° C., yield 2.3 g.

EXAMPLE 9

Production of 2-thiophenecarboxylic acid anilide

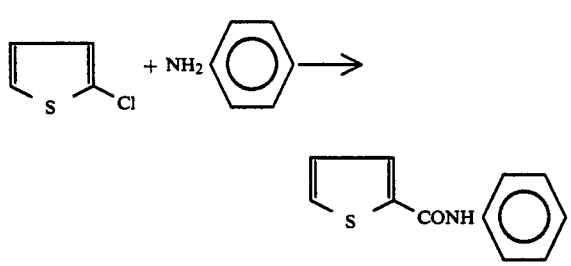

In an autoclave made of a metal were placed 7.12 g of 2-chlorothiophene, 1.86 g of aniline, 7.81 g of benzene, 17.5 mg of palladium chloride, 426 mg of bisdiphenylphosphinobutane and 2.33 g of carbon monoxide. The air in the autoclave was replaced with carbon monoxide introduced thereinto in several times, after which carbon monoxide was further introduced to adjust its pressure therein to 30 kg/cm$^2$. The bath temperature was adjusted to 225° C. on a salt bath and the reaction was carried thereon out with stirring for 3 hours. After completion of the reaction, the reaction mixture was cooled to room temperature and washed with water. Subsequently, the organic layer was separated and then concentrated to obtain 0.87 g of the desired compound 2-thiophenecarboxylic acid anilide.

Melting point 133°–141° C., yield 0.87 g.

EXAMPLE 10

Production of methyl ortho-α,α,α-trifluoromethylbenzoate

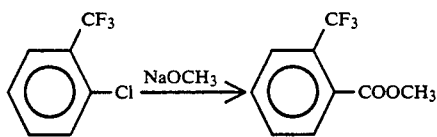

In an autoclave made of glass equipped with an electromagnetic induction type stirrer were placed 18.0 g of ortho-chlorobenzotrifluoride, 1.19 g of sodium methoxide, 3.5 mg of palladium chloride and 85.3 mg of bisdiphenylphosphinobutane. The air in the autoclave was replaced with carbon monoxide introduced thereinto in several times, after which carbon monoxide was further introduced to adjust its pressure therein to 30 kg/cm$^2$. The internal temperature was adjusted to 210° C. and the reaction was carried out thereon with stirring for 1.5 hours. After completion of the reaction, the reaction mixture was cooled to room temperature and washed with water. Subsequently, the organic layer was separated, concentrated, and then purified by a column chromatography to obtain 1.2 g of the desired compound methyl ortho-α,α,α-trifluoromethylbenzoate.

NMR:

| $\delta_{CDCl_3}^{TMS}$ (ppm) | 3.96(3H, s) |
|---|---|
| | 7.3–7.9(4H, m). |

Yield: 1.2 g.

EXAMPLE 11

Production of ethyl ortho-α,α,α-trifluoromethylbenzoate

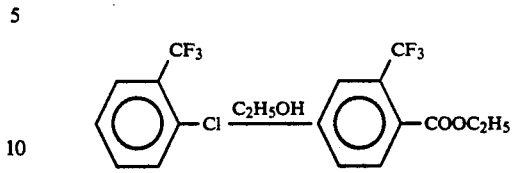

In an autoclave made of a metal were placed 18.0 g of ortho-chlorobenzotrifluoride, 4.6 g of ethanol, 17.5 mg of palladium chloride, 85.3 mg of bisdiphenylphosphinobutane and 2.3 g of sodium carbonate. The air in the autoclave was replaced with carbon monoxide introduced thereinto in several times, after which carbon monoxide was further introduced to adjust its pressure therein to 30 kg/cm$^2$. The internal temperature was adjusted to 200° C. on a salt bath and the reaction was carried out thereon with stirring for 5 hours. After completion of the reaction, the reaction mixture was cooled to room temperature and washed with water. Subsequently, the organic layer was separated and then concentrated to obtain 1.9 g of the desired compound ethyl ortho-α,α,α-trifluoromethylbenzoate.

NMR:

| $\delta_{CDCl_3}^{TMS}$ (ppm) | 1.36(3H, t), |
|---|---|
| | 4.32(2H, q), |
| | 7.37–7.80(4H, m). |

Yield: 1.9 g.

EXAMPLE 12

Production of 4-methoxyphenyl 2-trifluoromethylbenzoate

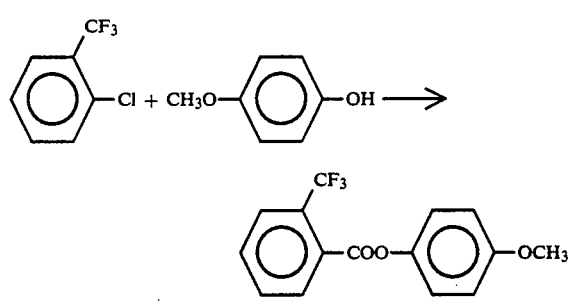

In an autoclave made of a metal were placed 45.13 g of ortho-chlorobenzotrifluoride, 6.2 g of para-methoxyphenol, 88.5 mg of palladium chloride, 213 mg of 1,4-bisdiphenylphosphinobutane and 5.3 g of sodium carbonate. The air in the autoclave was replaced with carbon monoxide introduced thereinto in several times, after which carbon monoxide was further introduced to adjust its pressure therein to 30 kg/cm$^2$. The internal temperature was adjusted to 190° C. on a salt bath and the reaction was carried out thereon with stirring for 5 hours.

After completion of the reaction, the reaction mixture was cooled to room temperature and washed with water. Subsequently, the organic layer was separated and then concentrated. Thus, 10.5 g of the desired ester was obtained.

Melting point 62°-63.50° C.

EXAMPLE 13

Production of 4-isopropylphenyl 2-trifluoromethylbenzoate

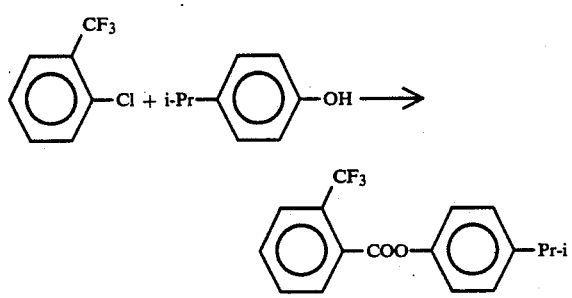

In an autoclave made of a metal were placed 45.13 g of ortho-chlorobenzotrifluoride, 6.8 g of paraisopropylphenol, 88.5 mg of palladium chloride, 213 mg of 1,4-bisdiphenylphosphinobutane and 5.3 g of sodium carbonate. The air in the autoclave was replaced with carbon monoxide introduced thereinto in several times, after which carbon monoxide was further introduced to adjust its pressure therein to 30 kg/cm$^2$. The internal temperature was adjusted to 190° C. on a salt bath and the reaction was carried out thereon with stirring for 4 hours.

After completion of the reaction, the reaction mixture was cooled to room temperature and washed with water. Subsequently, the organic layer was separated and then concentrated. Thus, 11.1 g of the desired ester was obtained.

Melting point 82.50°-84.50° C.

EXAMPLE 14

Production of 1,2,4-triethoxycarbonylbenzene

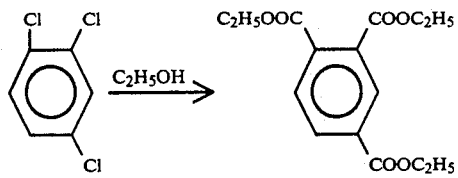

In an autoclave made of glass equipped with an electromagnetic induction type stirrer were placed 3.6 g of 1,2,4-trichlorobenzene, 4.6 g of ethanol, 5 ml of benzene, 17.8 mg of palladium chloride, 85.3 mg of bisdiphenylphosphinobutane and 2.3 g of sodium carbonate. The air in the autoclave was replaced with carbon monoxide introduced thereinto in several times, after which carbon monoxide was further introduced to adjust its pressure therein to 50 kg/cm$^2$. The internal temperature was adjusted to 200° C. and the reaction was carried out thereon with stirring for 3 hours. After completion of the reaction, the reaction mixture was cooled to room temperature and washed with water. Subsequently, the organic layer was separated, concentrated, and then concentrated by a column chromatography to obtain 1.62 g of the desired compound 1,2,4-triethoxycarbonylbenzene.

NMR:

| $\delta_{CDCl_3}^{TMS}$ (ppm) | 1.20-1.51(9H, m), |
|---|---|
| | 4.13-4.53(6H, m) |
| | 7.57-8.25(3H, m). |

Yield: 1.62 g,

EXAMPLE 15

Production of 1,2,4,5-tetraethoxycarbonylbenzene

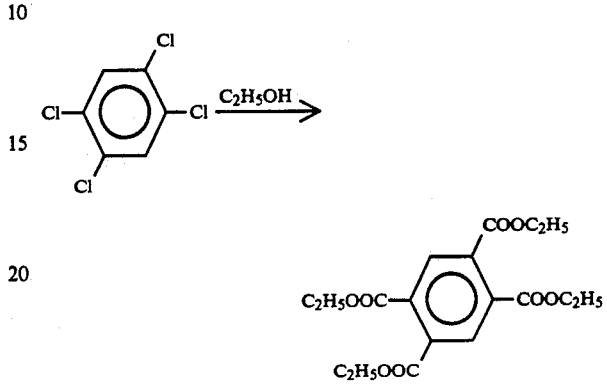

In an autoclave made of a metal were placed 1.08 g of 1,2,4,5-tetrachlorobenzene, 4.6 g of ethanol, 88 mg of palladium chloride, 106 mg of 1,4-bisdiphenylphosphinobutane, 4.2 g of sodium carbonate and 15 ml of benzene. The air in the autoclave was replaced with carbon monoxide introduced thereinto in several times, after which carbon monoxide was further introduced to adjust its pressure therein to 50 kg/cm$^2$. The internal temperature was adjusted to 200° C. on a salt bath and the reaction was carried out thereon with stirring for 3 hours. After completion of the reaction, the reaction mixture was cooled to room temperature, washed with water, concentrated, and then purified by a column chromatography to obtain 0.87 g of the desired compound 1,2,4,5-tetraethoxycarbonylbenzene.

NMR:

| $\delta_{CDCl_3}^{TMS}$ (ppm) | 1.38(12H, t), |
|---|---|
| | 4.37(8H, q), |
| | 8.00(2H, s). |

Yield: 0.87 g

EXAMPLE 16

Production of 4,4'-bis(ethoxycarbonyl)benzophenone

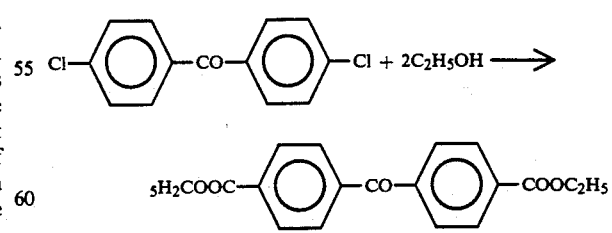

In an autoclave made of a metal were placed 2.51 g of 4,4'-dichlorobenzophenone, 4.61 g of ethanol, 8.7 mg of palladium chloride, 213 mg of 1,4-bisdiphenylphosphinobutane, 2.33 g of sodium carbonate and 30 ml of benzene. The air in the autoclave was replaced with carbon monoxide introduced thereinto in several times, after which carbon monoxide was further introduced to adjust its pressure therein to 50 kg/cm². The bath temperature was adjusted to 230° C. on a salt bath and the reaction was carried out thereon with stirring for 5 hours.

After completion of the reaction, the reaction mixture was cooled to room temperature and washed with water. Subsequently, the organic layer was separated and then concentrated. Thus, 2.33 g of the desired ester was obtained.

Melting point 74°–76° C.

EXAMPLE 17

Production of 4,4'-bis(ethoxycarbonyl)diphenylsulfone

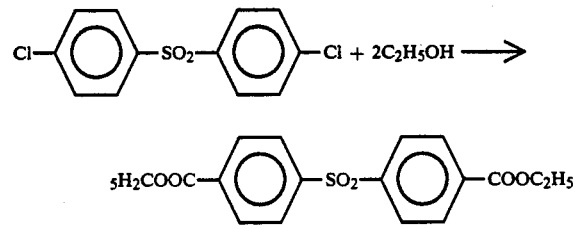

In an autoclave made of a metal were placed 2.87 g of 4,4'-dichlorodiphenylsulfone, 4.61 g of ethanol, 8.8 mg of palladium chloride, 213 mg of 1,4-bisdiphenylphosphinobutane, 2.33 g of sodium carbonate and 30 ml of benzene. The air in the autoclave was replaced with carbon monoxide introduced thereinto in several times, after which carbon monoxide was further introduced to adjust its pressure therein to 50 kg/cm². The bath temperature was adjusted to 200° C. on a salt bath and the reaction was carried out thereon with stirring for 3 hours.

After completion of the reaction, the reaction mixture was cooled to room temperature and washed with water. Subsequently, the organic layer was separated and then concentrated. Thus, 1.96 g of the desired ester was obtained.

Melting point 153°156° C.

EXAMPLE 18

Production of ethyl 2-thiophenecarboxylate

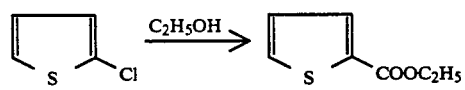

In an autoclave made of a metal were placed 2.4 g of 2-chlorothiophene, 4.6 g of ethanol, 5 ml of benzene, 17.8 mg of palladium chloride, 85.3 mg of bisdiphenylphosphinobutane and 2.3 g of sodium carbonate. The air in the autoclave was replaced with carbon monoxide introduced thereinto in several times, after which carbon monoxide was further introduced to adjust its pressure therein to 50 kg/cm². The bath temperature was adjusted to 250° C. on a salt bath and the reaction was carried out thereon with stirring for 3 hours. After completion of the reaction, the reaction mixture was cooled to room temperature and washed with water. Subsequently, the organic layer was separated, concentrated, and then purified by a column chromatography to obtain 1.0 g of the desired compound ethyl 2-thiophenecarboxylate.

NMR:

| $\delta_{CDCl_3}^{TMS}$ (ppm) | 1.35(3H, t), 4.27(2H, q), 6.88–7.73(3H, m). |
| --- | --- |

Yield: 1.0 g,

EXAMPLE 19

Production of ethyl nicotinate

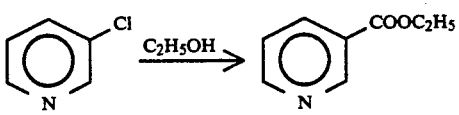

In an autoclave made of a metal were placed 2.3 g of 3-chloropyridine, 4.6 g of ethanol, 5 ml of benzene, 17.8 mg of palladium chloride, 85.3 mg of bisdiphenylphosphinobutane and 2.3 mg of sodium carbonate. The air in the autoclave was replaced with carbon monoxide introduced thereinto in several times, after which carbon monoxide was further introduced to adjust its pressure therein to 50 kg/cm². The bath temperature was adjusted to 250° C. on a salt bath and the reaction was carried out thereon with stirring for 3 hours. After completion of the reaction, the reaction mixture was cooled to room temperature and washed with water. Subsequently, the organic layer was separated, concentrated, and then purified by a column chromatography to obtain 0.46 g of the desired compound ethyl nicotinate.

NMR:

| $\delta_{CDCl_3}^{TMS}$ (ppm) | 1.41(3H, t), 4.38(2H, q), 7.18–7.40(1H, m), 8.12–8.28(1H, m), 8.60–8.72(1H, m), 9.08–9.13(1H, m). |
| --- | --- |

Yield: 0.46 g

EXAMPLE 20

Production of 4,7-diethoxycarbonylquinoline

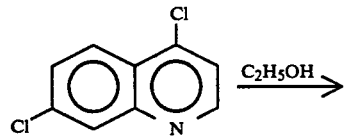

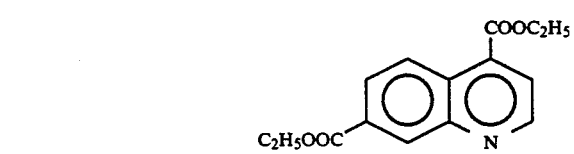

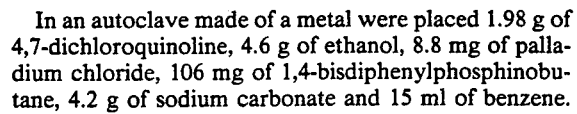

In an autoclave made of a metal were placed 1.98 g of 4,7-dichloroquinoline, 4.6 g of ethanol, 8.8 mg of palladium chloride, 106 mg of 1,4-bisdiphenylphosphinobutane, 4.2 g of sodium carbonate and 15 ml of benzene. The air in the autoclave was replaced with carbon monoxide introduced thereinto in several times, after which carbon monoxide was further introduced to adjust its pressure therein to 50 kg/cm². The internal temperature was adjusted to 200° C. on a salt bath and the reaction was carried out thereon with stirring for 3 hours. After completion of the reaction, the reaction mixture was cooled to room temperature, washed with water, concentrated, and purified by a column chromatography to obtain 0.87 g of the desired compound 4,7-diethoxycarbonylquinoline.

NMR:

| $\delta_{CDCl_3}^{TMS}$ (ppm) | 1.31–1.58(6H, m), |
|---|---|
| | 4.26–4.67(4H, m), |
| | 7.87–9.07(5H, m). |

Yield: 0.87 g

EXAMPLE 21

Production of 2,3-diethoxycarbonylpyridine

<chemical structure: 2,3-dichloropyridine + C₂H₅OH → 2,3-diethoxycarbonylpyridine>

In an autoclave made of a metal were placed 1.5 g of 2,3-dichloropyridine, 8.8 mg of palladium chloride, 106 mg of 1,4-bisdiphenylphosphinobutane, 4.2 g of sodium carbonate, 4.6 g of ethanol and 15 ml of benzene. The air in the autoclave was replaced with carbon monoxide introduced thereinto in several times, after which carbon monoxide was further introduced to adjust its pressure therein to 50 kg/cm². The bath temperature was adjusted to 250° C. on a salt bath and the reaction was carried out thereon with stirring for 3 hours. After completion of the reaction, the reaction mixture was cooled to room temperature, washed with water, concentrated, and then purified by a column chromatography to obtain 0.04 g of the desired compound 2,3-diethoxycarbonylpyridine.

NMR:

| $\delta_{CDCl_3}^{TMS}$ (ppm) | 1.27–1.57(6H, m) |
|---|---|
| | 4.16–4.62(4H, q) |
| | 6.73–6.97(1H, q) |
| | 7.98–8.30(2H, m). |

What is claimed is:

1. A process for producing a carboxylic acid ester represented by the general formula (I-2)

$$R^1\text{-}(COOR^4)_m \quad (I\text{-}2)$$

wherein $R^1$ is a phenyl or substituted phenyl group with substituents selected from the group consisting of halogen atom, alkyl group having 1 to 3 carbon atoms, haloalkyl group having 1 to 3 carbon atoms, cyano group, nitro group, hydroxy group, alkoxy group having 1 to 3 carbon atoms, alkylthio group having 1 to 3 carbon atoms, alkylcarbonyl group having 1 to 3 carbon atoms or amino group, said $R^1$ further being phenoxyphenyl group, benzoylphenyl group, phenylsulfonylphenyl group, biphenyl group, hydroxybiphenyl group, thienyl group, furyl group, pyridyl group, picolinyl group, quinolinyl group and quinoxalinyl group; $R^4$ is an alkyl group having 1 to 8 carbon atoms, phenyl group, cresyl group, xylenyl group, benzyl group, cinnamyl group, furfuryl group or thienyl group; and m is an integer of 1 to 4;

said process comprising the steps of reacting an aromatic chloride represented by the general formula (IV)

$$R^1\text{-}(Cl)_m \quad (IV)$$

wherein $R^1$ and m have the same meaning as defined above, carbon monoxide and an alcohol represented by the general formula (II)

$$R^4\text{OH} \quad (II)$$

wherein $r^4$ have the same meaning as defined above, in the presence of a base and catalysts consisting of a palladium compound and a phosphine compound having the general formula (V)

$$(R)_2P\text{-}X\text{-}P(R)_2 \quad (V)$$

wherein R is an alkyl group having 1 to 4 carbon atoms or a phenyl group, and X is an alkylene group having 1 to 6 carbon atoms, $$-CH_2-CH\underset{\underset{H_3C}{|}}{\underset{O}{|}}\overset{}{\underset{}{\times}}\underset{\underset{CH_3}{|}}{\underset{O}{|}}CH-CH_2-,$$

<chemical structure: ferrocene-based bridge>

$$-CH_2CH_2-P(\text{phenyl})-CH_2CH_2-,$$

or a binaphthyl group;

said reaction being conducted under conditions that temperature and pressure are sufficient to induce reaction.

2. A process for producing a carboxylic acid ester according to claim 1, wherein the palladium compound is metallic palladium, metallic palladium supported on a solid, or a zerovalent, divalent or tetravalent palladium complex.

3. A process for producing a carboxylic acid ester according to claim 1, wherein the palladium compound is palladium carbon, palladium chloride or palladium acetate.

4. A process for producing a carboxylic acid ester according to claim 1, wherein the base is an inorganic base or an organic base.

5. A process for producing a carboxylic acid ester according to claim 1, wherein the base is sodium carbonate or potassium carbonate.

6. A process for producing a carboxylic acid ester according to claim 1, wherein the reaction temperature is 100° to 300° C.

7. A process for producing a carboxylic acid ester according to claim 1, wherein the pressure of carbon monoxide is 1 to 200 atmospheres.

* * * * *